(12) United States Patent
Daly et al.

(10) Patent No.: US 12,064,159 B2
(45) Date of Patent: Aug. 20, 2024

(54) APPARATUS AND METHODS FOR IMPINGEMENT COOLING

(71) Applicant: Dominion Aesthetic Technologies, Inc., San Antonio, TX (US)

(72) Inventors: John G. Daly, Sorrento, FL (US); Matthew D. Hawk, Altamonte Springs, FL (US)

(73) Assignee: Dominion Aesthetic Technologies, Inc., San Antonio, TX (US)

( * ) Notice: Subject to any disclaimer, the term of this patent is extended or adjusted under 35 U.S.C. 154(b) by 51 days.

(21) Appl. No.: 17/738,255

(22) Filed: May 6, 2022

(65) Prior Publication Data
US 2022/0257300 A1    Aug. 18, 2022

Related U.S. Application Data

(63) Continuation of application No. 15/820,699, filed on Nov. 22, 2017.
(Continued)

(51) Int. Cl.
*A61N 5/06* (2006.01)
*A61B 18/02* (2006.01)
(Continued)

(52) U.S. Cl.
CPC .............. *A61B 18/02* (2013.01); *A61B 18/14* (2013.01); *A61B 18/18* (2013.01); *A61B 18/203* (2013.01);
(Continued)

(58) Field of Classification Search
CPC ...... A61N 5/0616; A61B 18/18; A61B 14/14; A61B 18/02
See application file for complete search history.

(56) References Cited

U.S. PATENT DOCUMENTS

| | | |
|---|---|---|
| 5,779,696 A | 7/1998 | Berry |
| 5,878,144 A | 3/1999 | Aucsmith |

(Continued)

FOREIGN PATENT DOCUMENTS

| | | |
|---|---|---|
| CA | 2646881 A1 | 9/2007 |
| DE | 10307260 A1 | 8/2003 |

(Continued)

OTHER PUBLICATIONS

AMS, "Color Sensors and Proximity Detection," 2012 (https://ams.com/documents/20143/36005/TCS3772_FS000111_1-00.pdf/c4fe790c-7faf-6b 1 f-3ae8-ada40622b2b6).
(Continued)

*Primary Examiner* — Sean W Collins
*Assistant Examiner* — Ryan T Clark
(74) *Attorney, Agent, or Firm* — Greenberg Traurig, LLP; Chinh H. Pham; Jose R. Vento

(57) ABSTRACT

A jet impingement cooling apparatus is provided including a housing having a surface to be directed at a treatment area, an optically transparent region on the surface of the housing through which electromagnetic radiation (EMR) from a source can be directed from the housing to the treatment area, and at least one opening on the surface of the housing through which a fluid flow can be directed to the treatment area to maintain the treatment area at a therapeutically acceptable temperature range while avoiding interference with the EMR being directed at the treatment area.

20 Claims, 18 Drawing Sheets

Related U.S. Application Data

(60) Provisional application No. 62/497,521, filed on Nov. 22, 2016, provisional application No. 62/497,535, filed on Nov. 22, 2016, provisional application No. 62/497,519, filed on Nov. 22, 2016.

(51) Int. Cl.
  *A61B 18/14* (2006.01)
  *A61B 18/18* (2006.01)
  *A61B 18/20* (2006.01)
  A61B 18/00 (2006.01)
  A61N 5/00 (2006.01)
  A61N 5/067 (2006.01)

(52) U.S. Cl.
  CPC .. *A61N 5/0616* (2013.01); *A61B 2018/00029* (2013.01); *A61N 2005/007* (2013.01); *A61N 5/067* (2021.08)

(56) References Cited

U.S. PATENT DOCUMENTS

| | | | |
|---|---|---|---|
| 5,968,033 A | 10/1999 | Fuller | |
| 6,080,146 A | 6/2000 | Altshuler | |
| 6,106,516 A | 8/2000 | Massengill | |
| 6,319,273 B1 | 11/2001 | Chen | |
| 6,361,495 B1 * | 3/2002 | Grolman | A61B 3/165 600/401 |
| 6,508,813 B1 | 1/2003 | Altshuler | |
| 6,517,532 B1 | 2/2003 | Altshuler | |
| 6,652,512 B2 | 11/2003 | Ota | |
| 6,653,618 B2 | 11/2003 | Zenzie | |
| 6,663,620 B2 | 12/2003 | Altshuler | |
| 6,878,144 B2 | 4/2005 | Altshuler | |
| 6,974,451 B2 | 12/2005 | Altshuler | |
| 6,976,985 B2 | 12/2005 | Altshuler | |
| 6,997,923 B2 | 2/2006 | Anderson | |
| 7,090,670 B2 | 8/2006 | Sink | |
| 7,276,058 B2 | 10/2007 | Altshuler | |
| 7,351,252 B2 | 4/2008 | Altshuler | |
| 7,540,869 B2 | 6/2009 | Altshuler | |
| 7,586,957 B2 | 9/2009 | Sierra | |
| 7,763,016 B2 | 7/2010 | Altshuler | |
| 7,856,985 B2 | 12/2010 | Mirkov | |
| 7,929,579 B2 | 4/2011 | Hohm | |
| 8,002,768 B1 | 8/2011 | Altshuler | |
| 8,028,536 B2 | 10/2011 | Morgan | |
| 8,317,779 B2 | 11/2012 | Mirkov | |
| 8,322,348 B2 | 12/2012 | Mirkov | |
| 8,328,794 B2 | 12/2012 | Altshuler | |
| 8,328,796 B2 | 12/2012 | Altshuler | |
| 8,540,869 B2 | 9/2013 | Zakarian | |
| 8,915,948 B2 | 12/2014 | Altshuler | |
| 8,992,516 B2 | 3/2015 | Muller | |
| 9,028,536 B2 | 5/2015 | Sierra | |
| 9,884,204 B1 | 2/2018 | Dolleris | |
| 10,500,413 B2 | 12/2019 | Altshuler | |
| 10,556,123 B2 | 2/2020 | Altshuler | |
| 10,994,151 B2 | 5/2021 | Daly | |
| 11,638,835 B2 | 5/2023 | Daly | |
| 2001/0053907 A1 | 12/2001 | Ota | |
| 2003/0060810 A1 | 3/2003 | Syrowicz | |
| 2005/0137658 A1 | 6/2005 | Hennings | |
| 2005/0154431 A1 | 7/2005 | Quistgaard | |
| 2006/0189976 A1 | 8/2006 | Karni | |
| 2006/0195166 A1 | 8/2006 | Minamoto | |
| 2006/0200116 A1 | 9/2006 | Ferren | |
| 2006/0271028 A1 | 11/2006 | Altshuler | |
| 2007/0161976 A1 | 7/2007 | Trembly | |
| 2007/0185553 A1 | 8/2007 | Kennedy | |
| 2007/0219605 A1 | 9/2007 | Yaroslavsky | |
| 2007/0282318 A1 | 12/2007 | Spooner | |
| 2008/0015555 A1 | 1/2008 | Manstein | |
| 2008/0071332 A1 | 3/2008 | Nelson | |
| 2009/0131922 A1 | 5/2009 | Dewey | |
| 2009/0182315 A1 | 7/2009 | Zigan | |
| 2009/0221999 A1 | 9/2009 | Shahidi | |
| 2010/0192596 A1 | 8/2010 | Quisenberry et al. | |
| 2010/0268220 A1 | 10/2010 | Johnson | |
| 2011/0060322 A1 | 3/2011 | Manstein | |
| 2012/0029499 A1 | 2/2012 | Bernabei | |
| 2012/0116373 A1 | 5/2012 | Moench | |
| 2012/0150520 A1 | 6/2012 | Vaillant | |
| 2012/0232536 A1 | 9/2012 | Liu | |
| 2012/0239016 A1 | 9/2012 | Liu | |
| 2013/0013032 A1 | 1/2013 | Irwin | |
| 2014/0025033 A1 | 1/2014 | Mirkov | |
| 2015/0265847 A1 | 9/2015 | Homer | |
| 2015/0313532 A1 | 11/2015 | Marinkovich | |
| 2016/0166150 A1 | 6/2016 | Vilenskii | |
| 2016/0270851 A1 | 9/2016 | Moench | |
| 2018/0140343 A1 | 5/2018 | Daly | |
| 2018/0140866 A1 | 5/2018 | Daly | |
| 2018/0271597 A1 | 9/2018 | Eisenmann et al. | |
| 2018/0303406 A1 | 10/2018 | Mckinney | |
| 2018/0353772 A1 | 12/2018 | Chen | |
| 2020/0391051 A1 | 12/2020 | Daly | |
| 2020/0406055 A1 | 12/2020 | Daly | |
| 2022/0265349 A1 | 8/2022 | Casalino et al. | |
| 2022/0273963 A1 | 9/2022 | Daly | |
| 2022/0273964 A1 | 9/2022 | Daly | |
| 2022/0401750 A1 | 12/2022 | Daly | |
| 2023/0093778 A9 | 3/2023 | Daly | |

FOREIGN PATENT DOCUMENTS

| | | |
|---|---|---|
| EP | 3415199 A1 | 12/2018 |
| JP | S56124451 U | 9/1981 |
| JP | 2002000745 A | 1/2002 |
| JP | 2004527330 A | 9/2004 |
| JP | 2005270125 A | 10/2005 |
| JP | 2008518661 A | 6/2008 |
| JP | 2009542330 A | 12/2009 |
| JP | 2010533569 A | 10/2010 |
| JP | 2011515201 A | 5/2011 |
| JP | 2020500072 A | 1/2020 |
| WO | 1999027863 A1 | 6/1999 |
| WO | WO-9927863 A1 * | 6/1999 |
| WO | 2002094116 A1 | 11/2002 |
| WO | 2008002625 A2 | 1/2008 |
| WO | 2014149021 A2 | 9/2014 |
| WO | 2016012584 A1 | 1/2016 |
| WO | 2018098274 A1 | 5/2018 |
| WO | 2018226995 A1 | 12/2018 |

OTHER PUBLICATIONS

Heintzmann, Rainer, "Appendix: Practical Guide to Optical Alignment," https://onlinelibrary.wiley.com/doi/pdf/10.1002/9783527671595.app1.
International Search Report in International Patent Application PCT/US2017/063001 mailed Jan. 30, 2018; By: Authorized Officer: Blaine R. Copenheaver.
International Search Report in International Patent Application PCT/US2017/063010 mailed Feb. 12, 2018; By: Authorized Officer: Lee W. Young.
International Search Report in International Patent Application No. PCT/US2020/037550, mailed Sep. 2, 2020; Lee Young.

* cited by examiner

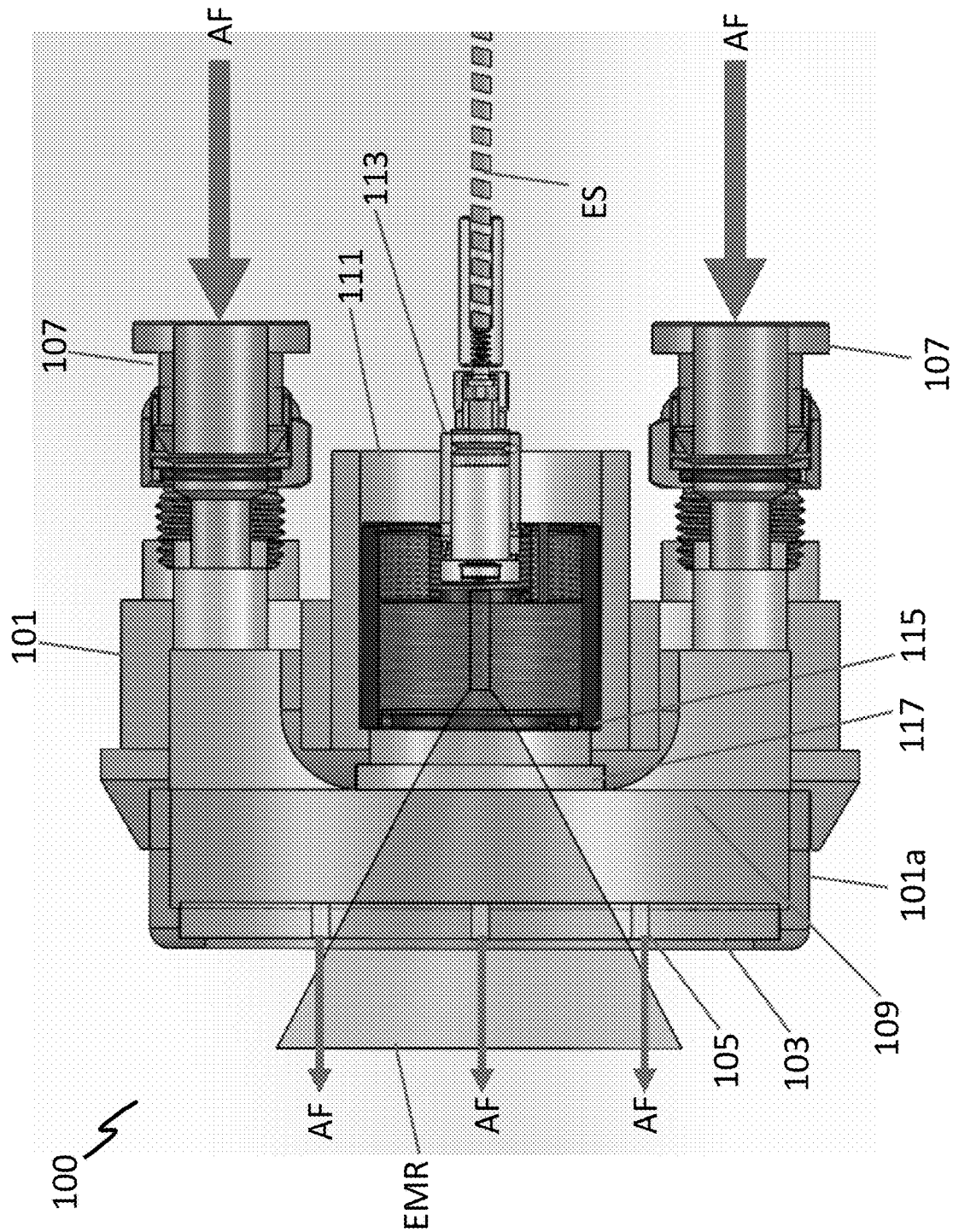

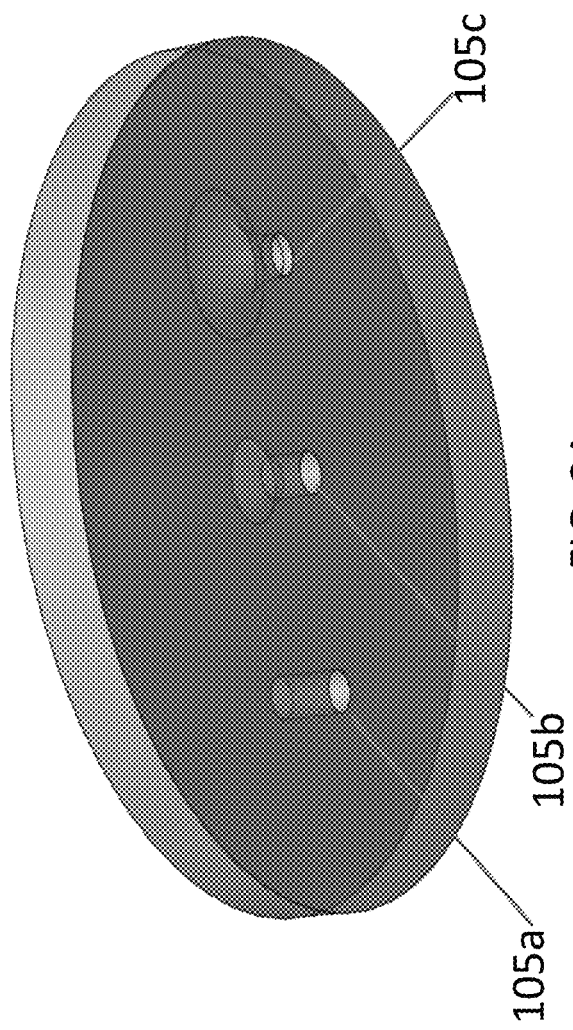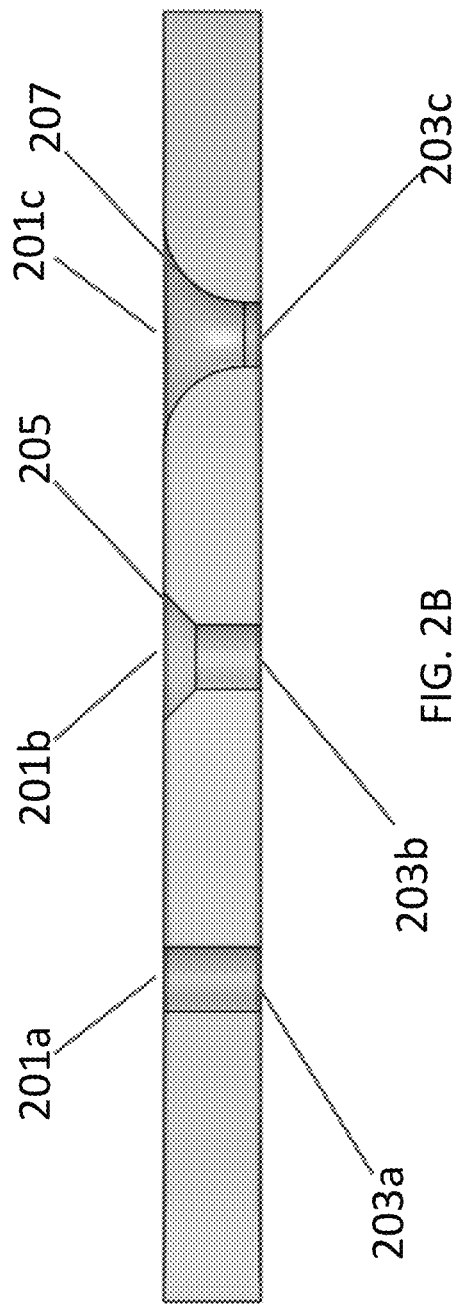
FIG. 2A
FIG. 2B

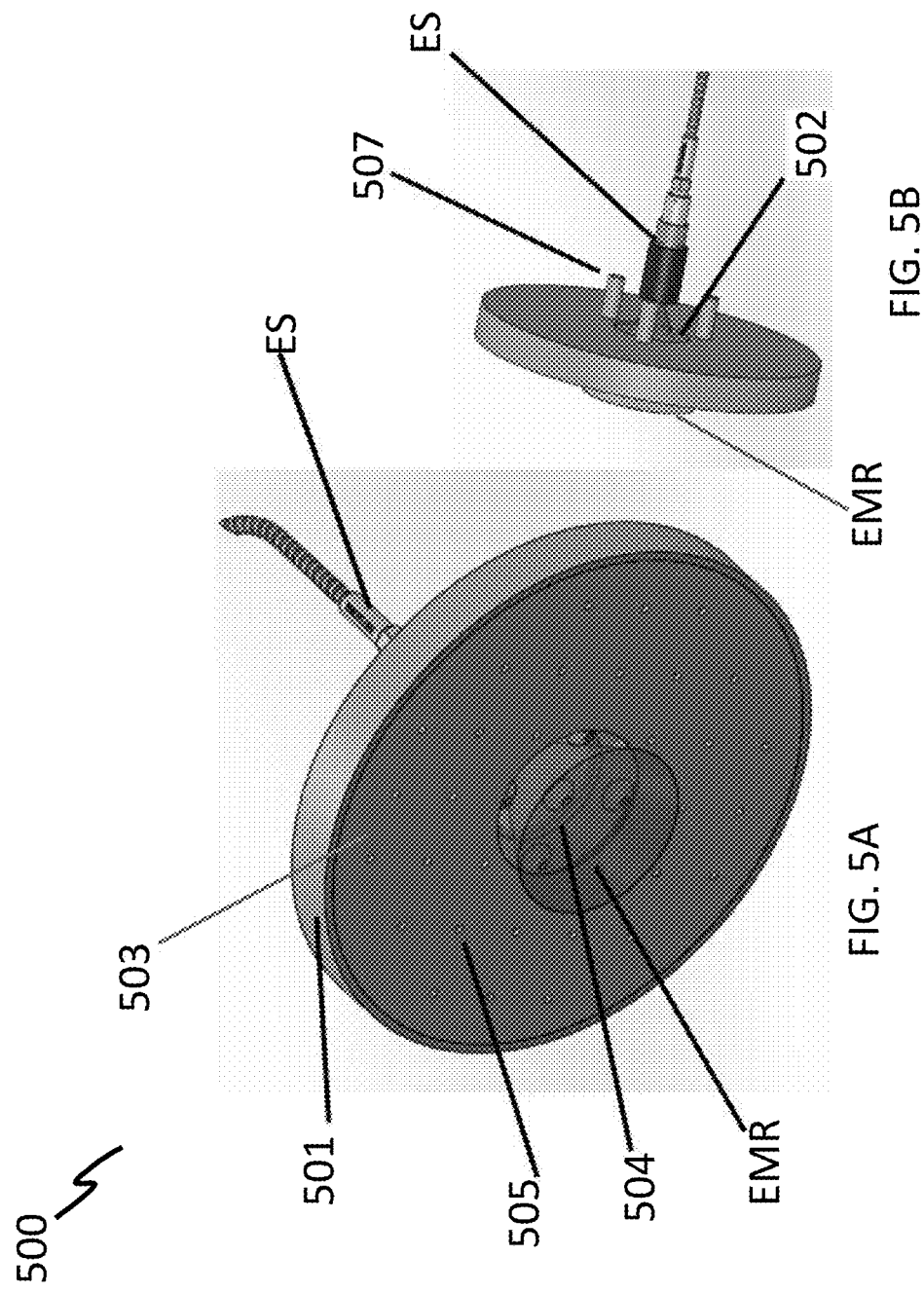

APPARATUS AND METHODS FOR IMPINGEMENT COOLING

RELATED APPLICATIONS

This application is a continuation application of U.S. application Ser. No. 15/820,699, filed Nov. 22, 2017, which claims the benefit of and priority to U.S. Provisional Application No. 62/497,535, filed Nov. 22, 2016, U.S. Provisional Application No. 62/497,521, filed Nov. 22, 2016, and 62/497,519, filed Nov. 22, 2016, all of which are incorporated herein by reference.

TECHNICAL FIELD

The present disclosure relates generally to cooling apparatus, and more particularly, to impingement cooling apparatus.

BACKGROUND

Skin cooling during hyperthermia treatment of tissues lying below the skin is designed to cool and protect the skin while allowing energy to pass through the skin to the underlying tissues. One conventional application uses light sources to produce energy that passes through an optically transparent but thermally conductive window material such as sapphire, which can be placed in contact with the skin for cooling. The perimeter of the thermally conductive sapphire window is then cooled with chilled water flowing through tubing passages. However, in such configurations, skin cooling is highly nonuniform, with good cooling around the periphery of the window, and less effective cooling toward the center of the window. Effective uniform skin cooling can also be hampered by poor or partial contact of the cold plate with the skin.

For short term applications in aesthetic skin treatments, another method involves cryogenic spray cooling. Droplets of liquid with low boiling point are applied in pulsed fashion to the skin region, dropping local temperatures just prior to application of laser energy. The refrigerant may vary, but a prime example includes R 134a with a −26° C. boiling point. Boiling of a refrigerant is highly effective heat transfer. However long term use over large patient areas required for certain aesthetic procedures introduces a host of practical difficulties. Some of ease-of-use difficulties include temperature control of skin area relative to refrigerant boiling point and complex set of variables associated with heat transfer. Refrigerant must also be replenished and frequent use introduces vapors which are a hazard concern in office air.

SUMMARY

In one embodiment, an impingement cooling apparatus is provided. The apparatus includes a housing having a surface to be directed at a treatment area. The apparatus also includes an optically transparent region on the surface of the housing through which electromagnetic radiation (EMR) from a source can be directed from the housing to the treatment area. The apparatus also includes at least one opening on the surface of the housing through which a fluid flow can be directed to the treatment area to maintain the treatment area at a therapeutically acceptable temperature range while avoiding interference with the EMR being directed at the treatment area.

In some embodiments, at least one of the openings is formed in the optically transparent region of the surface. In some embodiments, the fluid flow directed through the openings forms a plurality of fluid jets for impinging the treatment area. In some embodiments, the openings are positioned to permit the fluid jets to impinge on a portion of the treatment area irradiated by the EMR. In some embodiments, an exit velocity of the fluid jets is sufficient to minimize a thermal boundary layer formed on the treatment area. In some embodiments, the exit velocity is between 20 meters per second and 200 meters per second. In some embodiments, the opening includes an inlet and an outlet, the inlet and the outlet having a constant diameter. In some embodiments, the opening includes an inlet and an outlet, the inlet having a larger diameter than the outlet to reduce a pressure drop across the opening. In some embodiments, the fluid flow includes at least one of air, water, or combinations thereof. In some embodiments, the fluid flow is airflow.

In another embodiment, a method for cooling a surface is provided. The method includes receiving a fluid flow in a housing having a surface to be directed at a treatment area. The method also includes transmitting electromagnetic radiation from a source through an optically transparent region on the surface of the housing to the treatment area. The method also includes directing the fluid flow through at least one opening on the surface of the housing to the treatment area to maintain the treatment area at a therapeutically acceptable temperature range while avoiding interference with the electromagnetic radiation being directed at the treatment area.

In some embodiments, the step of directing the fluid flow through the openings further comprises forming a plurality of fluid jets for impinging the treatment area. In some embodiments, the step of forming further comprises exiting the fluid jets from the openings at an exit velocity sufficient to minimize a thermal boundary layer formed on the treatment area. In some embodiments, the exit velocity is between 20 meters per second and 200 meters per second. In some embodiments, the method also includes positioning the surface to cause the fluid jets to impinge on a portion of the treatment area irradiated by the EMR. In some embodiments, the step of positioning further comprises adjusting a spacing between the surface and the treatment area to maintain the therapeutically acceptable temperature. In some embodiments, the method also includes cooling the fluid flow. In some embodiments, the cooled temperature of the fluid flow is between zero (0) ° C. and 39° C. In some embodiments, the step of cooling the fluid flow further comprises adjusting a temperature of the fluid flow to maintain the therapeutically acceptable temperature. In some embodiments, the method also includes adjusting a flow rate of the fluid flow to maintain the therapeutically acceptable temperature.

BRIEF DESCRIPTION OF THE DRAWINGS

Illustrative, non-limiting example embodiments will be more clearly understood from the following detailed description taken in conjunction with the accompanying drawings.

FIG. 1B is a perspective view of the jet impingement cooling apparatus of FIG. 1A in accordance with an embodiment of the present invention.

FIG. 2A is a perspective view of three different jet impingement nozzle configurations in accordance with an embodiment of the present invention.

FIG. 2B is a cross-sectional view of the three different jet impingement nozzles of FIG. 2A in accordance with an embodiment of the present invention.

FIG. 5A is a perspective view of still another jet impingement cooling apparatus in accordance with an embodiment of the present invention.

FIG. 5B is a side view of the jet impingement cooling apparatus of FIG. 5A in accordance with an embodiment of the present invention.

DETAILED DESCRIPTION

Figure 1A:
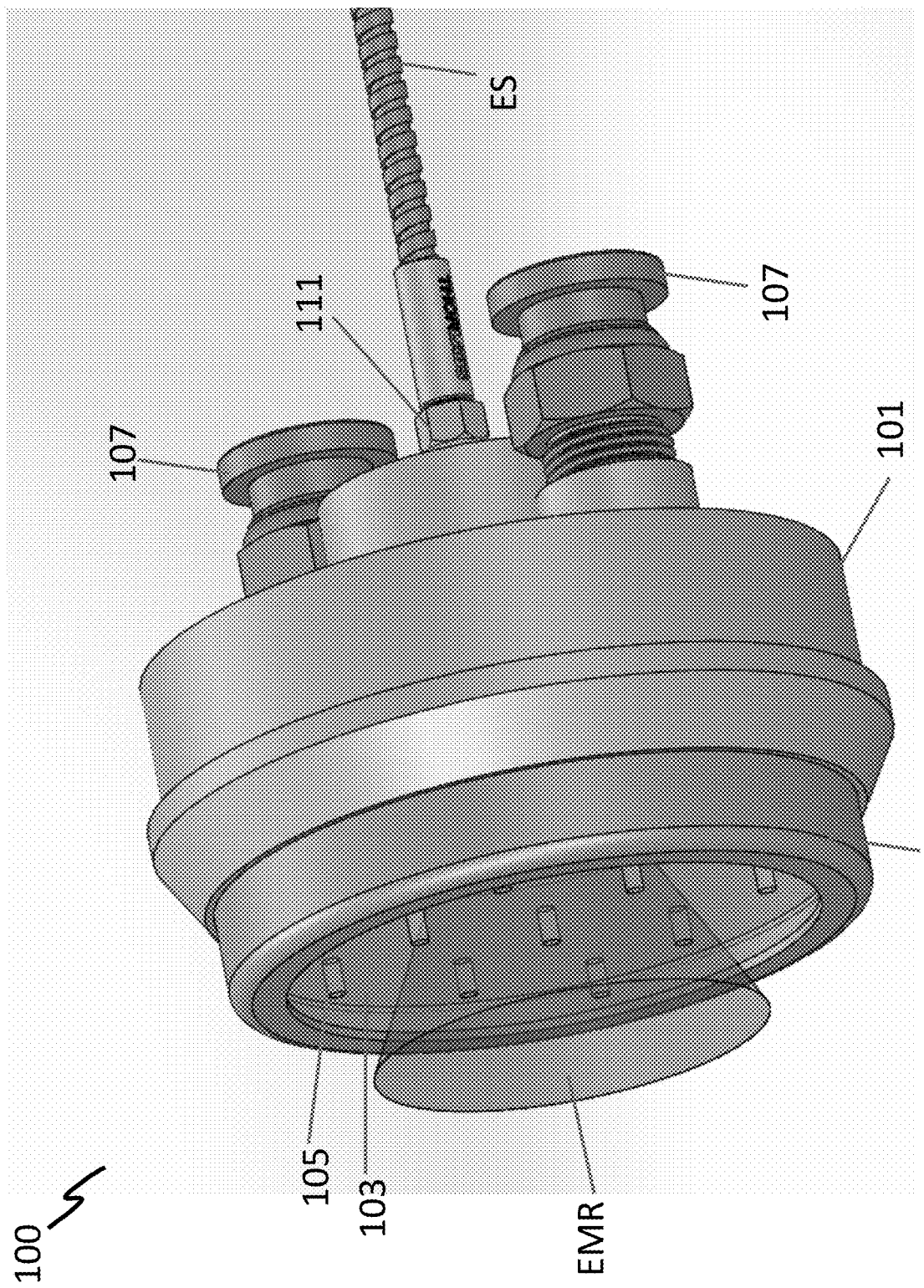
FIG. 1A is a perspective view of a jet impingement cooling apparatus in accordance with an embodiment of the present invention.

Various exemplary embodiments will be described more fully hereinafter with reference to the accompanying drawings, in which some example embodiments are shown. The present disclosure may, however, be embodied in many different forms and should not be construed as limited to the example embodiments set forth herein. Rather, these example embodiments are provided so that this disclosure will be thorough and complete, and will fully convey the scope of the present disclosure to those skilled in the art. In the drawings, the sizes and relative sizes of layers and regions may be exaggerated for clarity. Like numerals refer to like elements throughout.

Unless otherwise defined, all terms, including technical and scientific terms, used herein have the same meaning as commonly understood by one of ordinary skill in the art to which this disclosure belongs. For example, when an element is referred to as being "operatively engaged" with another element, the two elements are engaged in a manner that allows electrical and/or optical communication from one to the other.

Embodiments of the present disclosure generally provide jet impingement cooling apparatus. In some embodiments, the apparatus of the present disclosure can include a housing having a surface to be directed at a treatment area, a plurality of openings formed in the surface to permit airflow to be directed to a treatment area, and at least one optically transparent portion of the housing for permitting laser energy to be transmitted therethrough to the treatment area.

Referring now to FIG. 1A, a jet impingement cooling apparatus 100 is provided. The apparatus 100, in one embodiment, includes a housing 101 having a surface 103 to be directed at a treatment area. In order to retain an appropriate shape for airflow control and withstand stresses and forces associated with operation, the housing 101, in some embodiments, can be constructed of any suitable material such as metals, plastics, transparent plastics, glass, polycarbonates, polymers, sapphire, any other suitable material, or combinations thereof. To the extent that it is desirable to permit electromagnetic radiation (EMR) to be transmitted through the housing 101 to be directed to the treatment area, it may be advantageous to form at least a portion of the housing 101, in particular at least a portion of the surface 103, from an optically transparent material. In some embodiments, the housing 101, including the surface 103, can be entirely transparent. As shown in FIG. 1A, in some embodiments, at least a perimeter 101a of the housing 101 may be opaque to treatment wavelengths. Advantageously, the opaque portions, in some embodiments, can block EMR treatment energy from potential impingement onto the users or patient. Additionally, in some embodiments, a portion of the surface 103 through which EMR is not transmitted may not require transparent materials. Nevertheless, portions of the surface 103 proximate to or coincident with the EMR beam should generally be optically transparent so as not to interfere with transmission of the EMR.

The jet impingement cooling apparatus 100, as shown in FIG. 1A, can also include a plurality of openings 105 formed in the surface 103 for directing airflow onto the treatment area. Referring now to FIG. 1B, in some embodiments, the openings 105 can be positioned to direct the airflow AF onto the treatment area at temperatures, flow rates, and exit flow velocities suitable to maintain the treatment area at a therapeutically acceptable temperature range while avoiding interference with the EMR being directed at the treatment area. To that end, openings 105 coincident with or within close proximity to a portion of the surface 103 through which the EMR is transmitted (EMR transmission region) can be formed from optically transparent material. To the extent that other openings 105 are not aligned with the EMR transmission region, those openings may not need to be transparent.

In some embodiments, the plurality of openings 105 can be arranged in a pattern that can provide substantially uniform cooling over at least an entire treatment area of a target region, wherein the treatment area is the portion of the target region illuminated by the EMR. In some embodiments, the substantially uniform cooling can extend over an area larger than the treatment portion of the target surface. In such embodiments, pre and post cooling to the treatment area is permitted as the treatment device is moved from one treatment area to another, whether manually or by an automated mechanism programmed to deliver the appropriate energy to maintain the target temperature range for a procedure.

Generally, factors in maintaining efficient cooling of the treatment area include exit velocity of the impingement jets, spacing between outlets of the openings 105 and the treatment area, temperature of the cooling air, and positioning of the openings 105 relative to one another. In some embodiments, to maintain efficient cooling, the exit velocity of impingement jets exiting the openings 105 can be sufficient to minimize a thermal boundary layer of the treatment area, remove the thermal boundary layer, and/or to prevent formation of the thermal boundary layer. For example, in some embodiments, an exit velocity of the impingement jets of about 20 meters per second to about 200 meters per second can be sufficient to minimize or remove a thermal boundary layer while providing a sufficient flow rate for maintaining a therapeutically acceptable temperature of the treatment area. To the extent a particular exit velocity of the impingement jets of the plurality of openings 105 is desired, the exit velocity can be determined according to the relationship between a total supply air flow rate and a total aggregated outlet area of each opening 105. In one particular example, using one particular embodiment of the apparatus 100 having 9 orifice holes as shown in FIGS. 1A and 1B, if each opening 105 includes an outlet having a 0.2286 cm diameter and, thus, an area of 0.04129 square cm, the apparatus 100 would have a total aggregated outlet area of 9×0.04129=0.3697 square cm. Thus, for a cooling air supply flow rate of, for example, 169.9 liters per minute LPM, the resulting exit velocity from each opening is about 76 meters per second. However, it will be apparent in view of this disclosure that this is only one particular example and that, in accordance with various embodiments, any number of openings 105 having any size, shape, outlet area, total aggregated outlet area, or combinations thereof can be used to direct an airflow having any flow rate.

Assuming a constant opening 105 outlet size, spacing between the outlet of the opening and the treatment area, and cooling air temperature, the addition or subtraction of openings 105 will thus reduce or increase the exit velocity. For a constant number of openings 105, spacing between the outlet of the opening and the treatment area, and cooling air temperature, in order to increase the cooling capacity, exit velocity can be increased. In order to support the increased exit velocity, the flow rate of the cooling air introduced to the housing 101 and directed through the openings 105 can be increased.

In order to promote a uniform flow and maintain a desired cooling rate, during use, the openings 105 can be spaced apart from the target surface to maintain the substantially uniform cooling and to promote efficient jet impingement cooling. In particular, the proximity of the outlets of the openings 105 to the treatment area affects impingement velocity and flow characteristics of the impingement jets and can scale with the overall impingement geometry. With respect to cooling efficiency, in general, closer spacing results in greater cooling efficiency so long as the presence of the apparatus 100 does not interfere with the flow pattern and/or the ability to provide uniform flow over the treatment area. For example, assuming a constant exit velocity and cooling air temperature, increasing a spacing between the outlets and the treatment area from about 0.5 inches to about 0.75 inches results in a cooling efficiency loss of approximately 15%. In some embodiments, the spacing between the openings 105 and the target surface can be maintained in a range between 0.001 inches to more than an inch. In some embodiments, the spacing can be about 0.5 inches. More generally, any spacing between the openings 105 and the target surface can be used so long as substantially uniform cooling can be provided to the treatment area to maintain a therapeutically acceptable temperature range.

With respect to relative positioning of the openings 105, a tighter pattern, that is, decreasing the spacing between openings 105 and/or increasing the number of openings 105 formed in a surface 103 of constant size, can increase cooling efficiency. For example, decreasing spacing between the openings 105 such that spacing between the jets impinging on the treatment area is reduced from 0.8 inches to 0.6 inches can increase cooling efficiency by about 15%. With respect to cooling air temperature, cooling efficiency generally increases as temperature is reduced. For example, reducing the cooling air temperature from about 5° C. to about 0° C. can increase cooling efficiency by about 25%.

In some embodiments, the openings 105 can be configured to have any suitable internal geometry. For example, as shown in FIG. 2A a surface 103 is provided having three openings 105a, 105b, 105c formed therein, each having an inlet 201a, 201b, 201c and an outlet 203a, 203b, 203c. As shown in FIG. 2A, each opening 105a, 105b, 105c includes a different internal geometry and inlet size 201a, 201b, 201c while having a similar outlet 203a, 203b, 203c diameter. Referring now to FIG. 2B, the first opening 105a is a cylinder shape where the inlet 201a and outlet 203a diameters are substantially similar. The second opening 105b includes chamfer 205 proximate the inlet 201b, which, due to the chamfer 205, is larger than the outlet 203b. The third opening 105c includes a nozzle-shaped taper 207 extending from the inlet 201c and converging toward the outlet 203c. In general, because the diameter of the outlets 203a, 203b, 203c of the openings 105a, 105b, 105c are substantially similar, calculated exit velocity should be substantially similar for each of the openings 105a, 105b, 105c. However, some losses are associated with a pressure drop across the openings 105a, 105b, 105c. Thus, because the chamfer 205 of the second opening 105b and the nozzle-shaped taper 207 of the third opening 105c reduce the pressure drop by providing a more gradual flow constriction, the exit velocity of the second and third openings 105b, 105c will exceed the exit velocity of the first opening 105a.

Additionally, although the openings 105a, 105b, 105c, inlets 201a, 201b, 201c, and outlets 203a, 203b, 203c are each shown and described in FIGS. 1A and 2A as having a circular cross-section, it will be apparent in view of this disclosure that, in some embodiments, the openings 105a, 105b, 105c, inlets 201a, 201b, 201c, and outlets 203a, 203b, 203c can have any suitable cross-sectional shape. For example, cross-sectional shapes can include, but are not limited to, circular, square, rectangular, elliptical, oval, triangular, hexagonal, octagonal, any other suitable shape, or combinations thereof.

Figure 3:
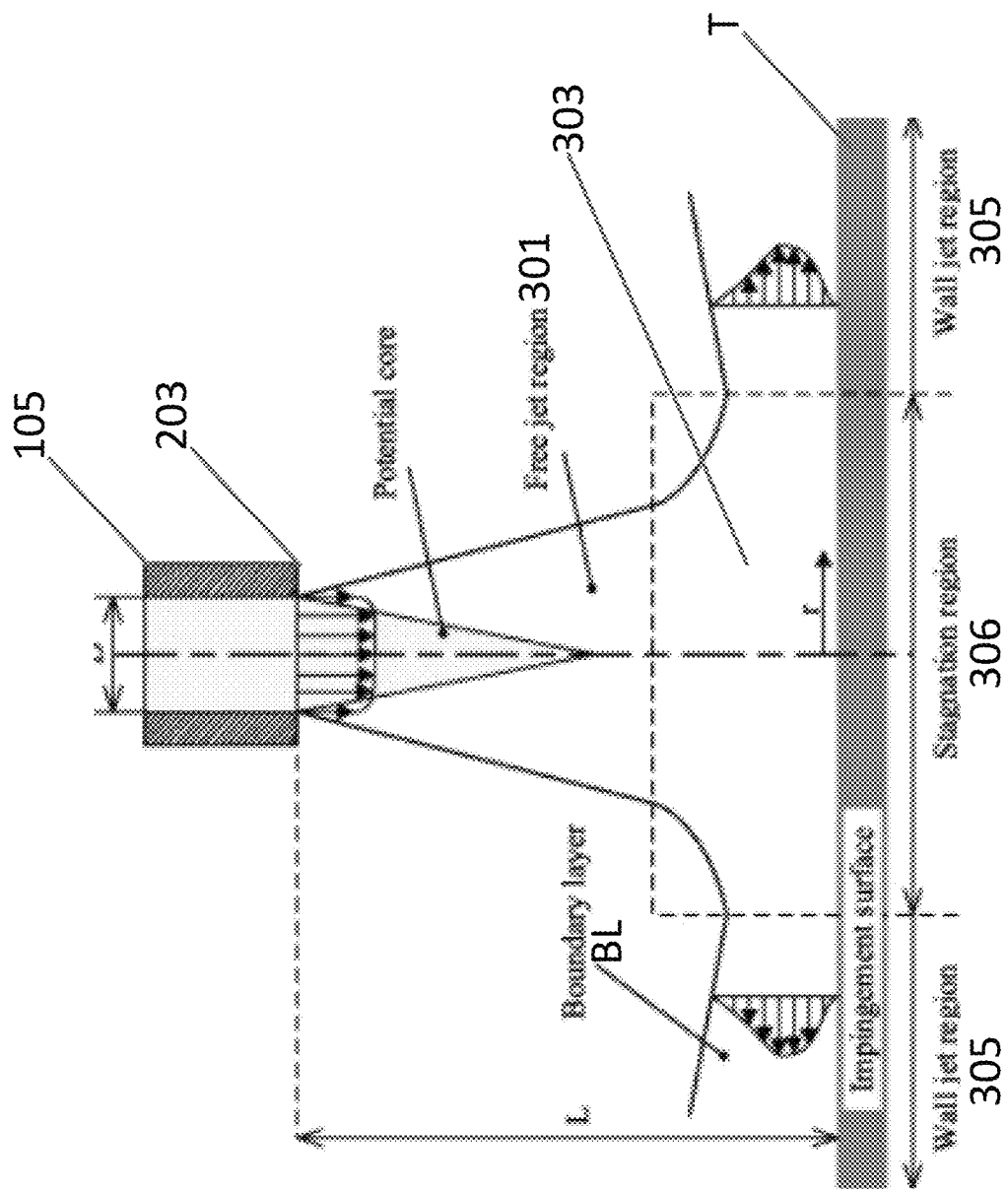
FIG. 3 illustrates a jet impingement cooling airflow pattern in accordance with an embodiment of the present invention.

Referring now to FIG. 3, generally, the outlet 203 of each opening 105 can direct the airflow to produce the impingement jets at an exit velocity sufficient to minimize a thermal boundary layer BL of the treatment area T so as to promote maintaining the treatment area T at the therapeutically acceptable temperature. In particular, FIG. 3 illustrates a flow map for airflow exiting an opening 105. As shown in FIG. 3, the outlet 203 of the opening 105 establishes a free jet region 301 and an impingement region 303 wherein the airflow of the free jet region 301 has minimized the thermal boundary layer BL. In the impingement region 303, upon impingement through the thermal boundary layer BL onto the treatment area T, the airflow can be redirected to a wall jet region 305 to further spread the cooling effects on along the surface of the treatment area. Generally, heat transfer is highest towards the center stagnation region 306 and diminishes gradually in the wall region 305.

By providing the impingement jets with high exit velocity, the thermal boundary layer BL can be substantially minimized in the treatment area, resulting in a higher surface heat transfer rate than for non-minimized boundary layer BL conditions. Therefore, cooling efficiency can generally be improved by providing higher exit velocities. As discussed above, exit velocity can generally be controlled by adjusting the total aggregated outlet 203 area of the openings 105 and/or the cooling air supply flow rate.

As also discussed above, cooling efficiency can also be adjusted by controlling a spacing between the outlet 203 and the treatment area T as well as by adjusting cooling air temperature. To the extent that one or more sensors are available for monitoring a temperature of the treatment area T, in some embodiments, the apparatus 100 can permit adjustment of the cooling air supply flow rate, the cooling air temperature, the spacing between the outlet 203 and the treatment area T, or combinations thereof in real time responsive to sensor feedback to maintain the therapeutically acceptable temperature.

Referring again to FIG. 1A, the apparatus 100, in some embodiments, can also include one or more cold air ports 107 for receiving airflow AF into the apparatus 100. Each port 107 can be any suitable design, size, or shape for connecting to an airflow source, including, for example, an opening in the housing 101, a tube in fluid communication with the housing, a luer lock connector, a fitting, any other suitable design, or combinations thereof. In some embodiments, the port 107 can be formed integrally with the housing 101. In some embodiments, the port can be a separate element attached to, fastened to, or otherwise in fluid communication with the housing 101.

In some embodiments, as shown in FIG. 1B, to distribute the airflow delivered through the port 107 to the openings 105, the housing 101 can also include a plenum 109 defined therein. The plenum 109 can act as a reservoir for collecting and substantially uniformly distributing the airflow AF throughout an interior of the housing 101 to be redirected to the openings 105. Thus, the plenum 109 can be in fluid communication with the port 107 and the openings 105 of the surface 103 to distribute the airflow delivered through the port 107 to the openings 105 in a substantially uniform manner. Accordingly, the plenum 109 can be configured to provide substantially uniform flow through each of the openings 105 and onto the treatment area. In some embodiments, the plenum 109 may include internal baffling (not shown) as required to provide a substantially uniform airflow output across all the openings 105 of the apparatus 100.

In some embodiments, the apparatus 100 can also include an EMR port 111 for permitting an EMR source ES to emit EMR through the EMR transmission region of the surface 103 for treatment of the treatment area. In some embodiments, the EMR source ES can include, for example, a laser source, an RF source, a fiber optic cable, a flashlamp source, an x-ray source, any other suitable source of EMR or EMR pathway, or combinations thereof. In some embodiments, as shown in FIG. 1B, the EMR source ES can be coupled to an EMR beam collimator 113 for homogenizing the EMR beam emitted by the EMR source ES.

In some embodiments, the collimator 113 can be incident on an optical element 115 such as a beam expander and/or other beam shaping optical elements to provide a desired EMR beam shape on the treatment area. In particular, because, as shown in FIG. 1B, the EMR is emitted in an expanding manner, the EMR beam is relatively narrow proximate to an input window 117 of the housing 101 where EMR from the EMR source ES is introduced. The EMR beam then expands in size the further it travels and illuminates the treatment area over an expanded, relatively large area. In some embodiments, the beam expansion can be configured to minimize a number of openings 105 intersected by the beam, thereby minimizing optical losses from any reflection or scattering caused by the opening 105 formed in the transparent transmission region of the surface 103. Although shown in FIGS. 1A and 1B as being a diverging EMR beam, it will be apparent in view of this disclosure that any beam shape can be used in accordance with various embodiments including, for example, a collimated beam, a focused beam, a converging beam, an expanding beam, a straightened expanded beam, etc. may be used as well with similar impingement jet cooling. In addition, although FIGS. 1A and 1B illustrate a single EMR beam being transmitted concentric with the housing 101, it will be apparent in view of this disclosure that, in some embodiments, any number of EMR beams can be transmitted through the housing 101 concentrically, non-concentrically, at an incident angle relative to the housing 101, or along any other suitable beam path.

In some embodiments, by providing a pattern of the openings 105 in the surface 103 larger than an impingement footprint of the expanded beam, the apparatus 100 can also provide substantially uniform cooling not just over the full treatment area irradiated by the EMR beam, but also in an annulus surrounding the treatment area. Such additional cooling can advantageously provide cooling to adjacent areas susceptible to being irradiated by stray EMR energy diverted due to EMR beam scattering and/or divergence. Furthermore, such adjacent cooling can also advantageously provide pre and post treatment cooling for treatment protocols wherein the EMR beam is scanned across the treatment area.

Figure 4A:
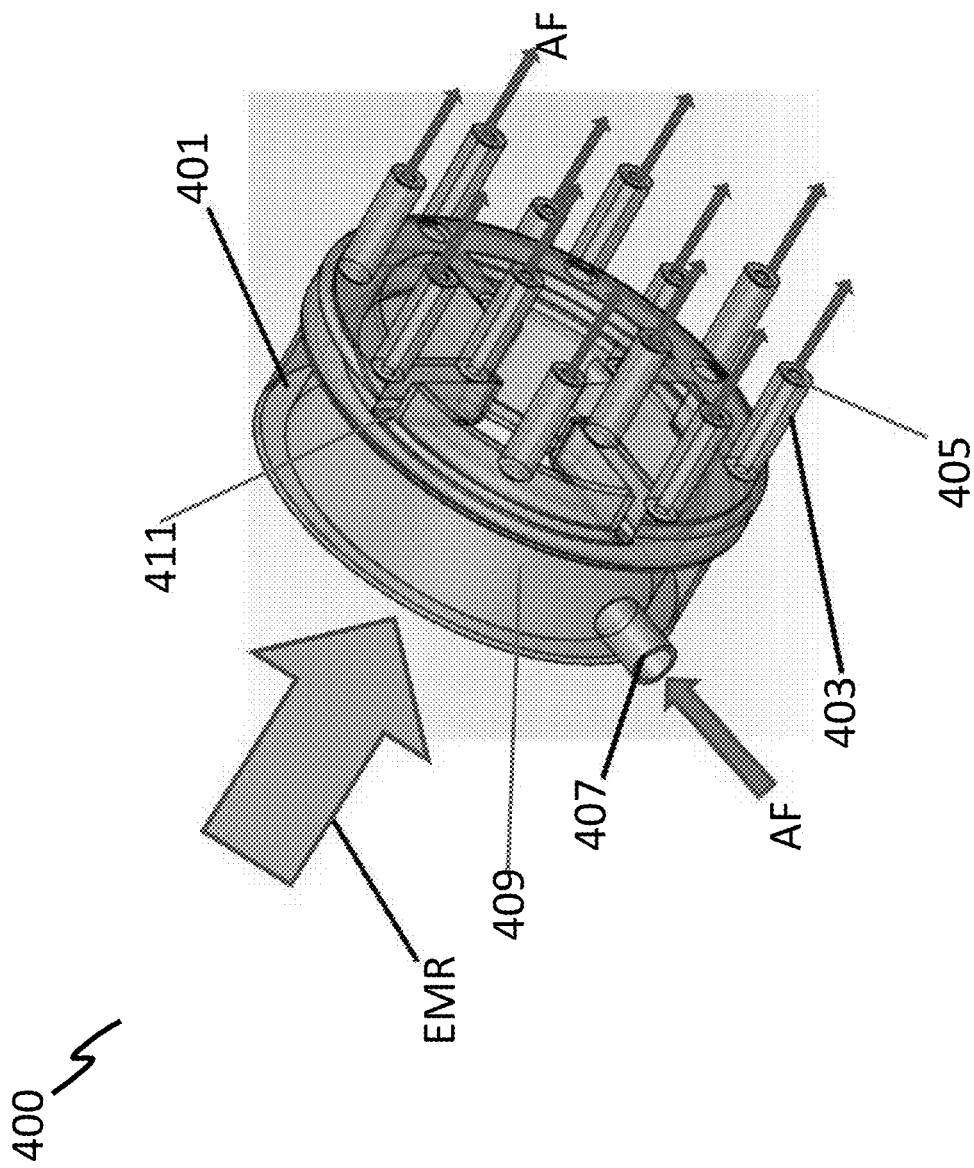
FIG. 4A is a perspective view of another jet impingement cooling apparatus in accordance with an embodiment of the present invention.

Referring now to FIG. 4A, in another embodiment, a jet impingement cooling apparatus 400 can include a housing 401 configured to minimize encroachment of airflow features on a transmission path of the EMR. The housing 401 can be, for example, but not limited to, constructed of similar materials to housing 101 described above with reference to FIG. 1 as required to provide appropriate airflow and EMR transmission characteristics onto the treatment area.

Still referring to FIG. 4A, the housing 401 can further include a port 407 for delivering airflow into a plenum 409 of the housing 401. In some embodiments, the port 407 and the plenum 409 can be, for example, substantially similar to the port 107 and plenum 109 described above with reference to FIG. 1. In some embodiments, the plenum 409 can include a plurality of baffles 411 formed in the housing for assisting in distributing airflow AF received via the port 407 substantially uniformly to a plurality of air tubes 403.

Figure 4B:
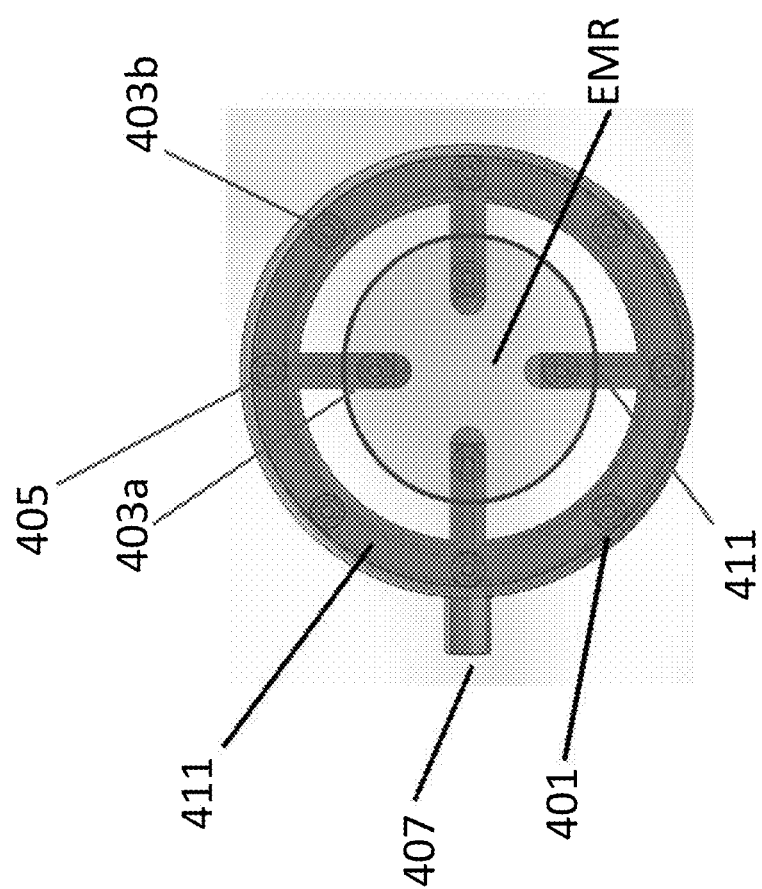
FIG. 4B is a bottom view of the jet impingement cooling apparatus of FIG. 4A in accordance with an embodiment of the present invention.

As shown in FIG. 4A, in some embodiments, the air tubes 403 can extend toward the treatment area from the baffles 411 of the housing 401 to direct airflow AF to the treatment area. Additionally, each air tube 403 can include an opening 405 therein through which the airflow AF can be directed to the treatment area. The openings 405, in accordance with various embodiments, can be, for example, substantially similar to the openings 105 as described above with reference to FIGS. 1 and 2. In some embodiments, the air tubes 403 can be positioned to direct the airflow AF through the openings 405 onto the treatment area at temperatures, flow rates, and exit flow velocities suitable to maintain the treatment area at a therapeutically acceptable temperature range while minimizing interference with EMR being directed at the treatment area. To that end, referring now to FIG. 4B, aligned air tubes 403a coincident with or within close proximity to a region of the housing 401 through which the EMR is transmitted (EMR transmission region), as well as the baffles 411 from which the aligned air tubes 403a extend, can be formed from optically transparent material. Additionally, the number of aligned air tubes 403a coincident with or within close proximity to the EMR transmission region can be minimized and configured to occupy as little of the EMR transmission region as possible while still providing substantially uniform cooling of the treatment area. Thus, in some embodiments, a majority of the EMR transmission region can be entirely unobstructed. Other air tubes 403b which are not coincident or proximate to the EMR transmission region may not need to be transparent. In some embodiments, the plurality of air tubes 403 can be positioned to provide substantially uniform cooling over at least an entire treatment area of a target region, wherein the treatment area is the portion of the target region illuminated by the EMR. In some embodiments, the substantially uniform cooling can extend over an area larger than the treatment area of the target surface to permit pre and post cooling of the treatment area. In order to promote a uniform flow and maintain a desired cooling rate, during use, the air tubes 403 can be spaced apart from the target surface to maintain the substantially uniform cooling and to promote efficient jet impingement cooling as described above with reference to FIGS. 1-3.

Referring now to FIG. 5A, in another embodiment, a jet impingement cooling apparatus 500 can include a housing 501, a majority of which is opaque to treatment wavelengths to block EMR treatment energy from potential impingement onto the users or non-treatment areas of the patient. To that end, the housing 501 can be, for example, but not limited to, constructed of similar materials to housing 101 described above with reference to FIG. 1 as required to block EMR treatment energy outside of the EMR transmission region.

The apparatus 500 can include a substantially opaque housing 501, including an EMR input surface 501a and an opposing surface 503 for being directed at a treatment area. To the extent that it is desirable to provide an EMR transmission region of the housing 501 to permit EMR to be transmitted through the input surface 501a of the housing 501 and the opposing surface 503 so as to be directed to the treatment area, the EMR input surface 501a can include an optically transparent input window 502 for permitting EMR delivered from an EMR source ES to be transmitted therethrough. Additionally, the opposing surface 503 can include an optically transparent output window 504 for permitting EMR transmitted through the input window 502 to be transmitted therethrough and thus directed to the treatment area. To facilitate EMR transmission therethrough, the input window 502 and the output window 504 can be constructed of any suitable optically transparent material including, for example, transparent plastics, glass, polycarbonates, sapphire, any other suitable optically transparent material, or combinations thereof The apparatus 500 can also include a plurality of openings 505 formed in the opposing surface 503 and the output window 504 for directing airflow onto the treatment area. Each of the plurality of openings 505 can be constructed, for example, substantially similar to the openings 105 described above with reference to FIGS. 1 and 2. The apparatus 500 can also include at least one cold air port 507 for receiving airflow into the housing 501. As shown in FIG. 5B, in one embodiment, the apparatus 500 can include three cold air ports 507 to provide more uniform distribution of the delivered cold air. Each cold air port 507 can be constructed, for example, substantially similar to the cold air port 107 described hereinabove with reference to FIG. 1.

Figure 6:
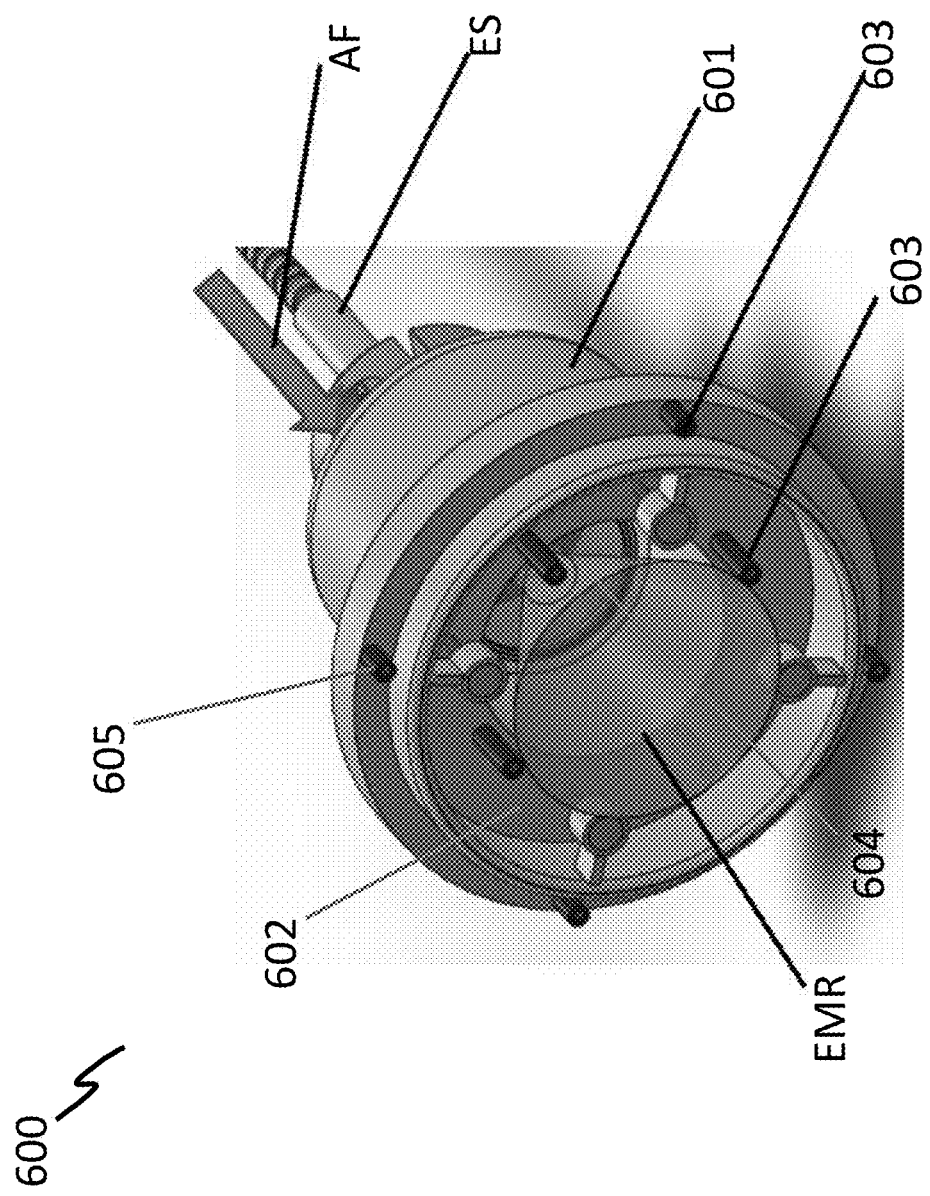
FIG. 6 is a perspective view of yet another jet impingement cooling apparatus in accordance with an embodiment of the present invention.

Referring now to FIG. 6, in another embodiment, a jet impingement cooling apparatus 600 can be provided to avoid placement of air tubes 603 in an EMR transmission region of the housing 601. The housing 601 can include one or more recesses 602 defined therein from which air tubes 603 can extend adjacent to, but not within, the EMR transmission region and still direct the airflow to impinge on the treatment area illuminated by the EMR. In particular, because the EMR is emitted in an expanding manner, the EMR beam is relatively narrow proximate to an input window 604 of the housing 601 where EMR from an EMR source ES is introduced. The EMR beam then expands in size the further it travels and illuminates the treatment area over an expanded, relatively large area. Thus, although the air tubes 603 are adjacent to, but not within, the EMR transmission region in the housing 601, the air jets produced by the openings 605 of the air tubes 603 can impinge on the treatment area coincident with the portions illuminated by the EMR. Additionally, in some embodiments, the housing 601 can include a plenum (not shown) surrounding the input window to provide substantially uniform distribution of feed airflow AF received therein.

In order to preserve airflow characteristics and withstand operational requirements, the housing 601 can be, for example, but not limited to, constructed of similar materials to housing 101 described above with reference to FIG. 1. The air tubes 603 and openings 605 can be, for example, similar to the air tubes 403 and openings 405 discussed above with reference to FIGS. 4A and 4B.

Figure 7:
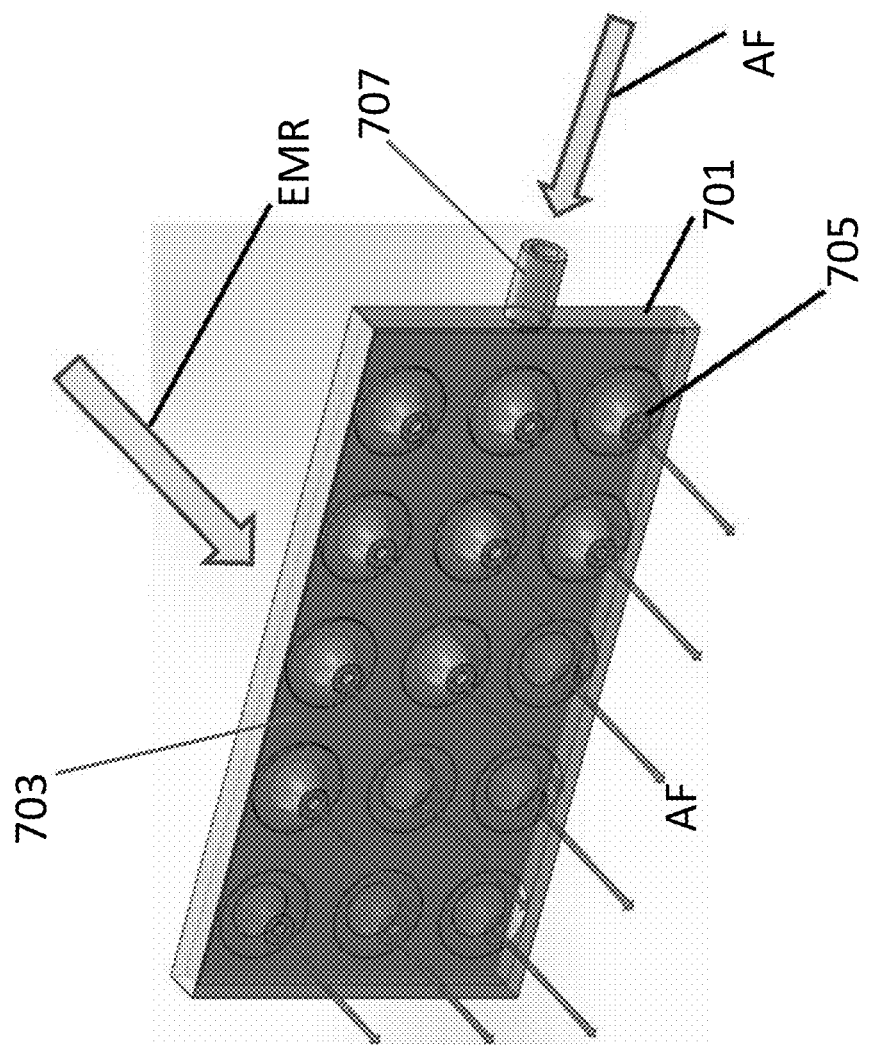
FIG. 7 is a perspective view of a rectangular jet impingement cooling apparatus in accordance with an embodiment of the present invention.

To facilitate a scanning treatment pattern over a particularly large treatment area, as shown in FIG. 7, a jet impingement cooling apparatus 700 can be provided having a rectangular housing 701. The housing including a surface 703 to be directed at a treatment area. To the extent that EMR is to be transmitted through the housing 701 to be directed to the treatment area, the housing 701, in some embodiments, can be at least partially constructed of an optically transparent material. The apparatus 700, as shown in FIG. 7 can include a plurality of openings 705 formed in the surface 703 for directing airflow AF onto the treatment area. Still referring to FIG. 7, the apparatus 700 can further include a cold air port 707 for receiving airflow AF into the housing 701 to be directed through the openings 705. In some embodiments, each of the housing 701, the surface 703, the openings 705, and the port 707 can be, for example, substantially similar to the housing 101, surface 103, openings 105, and port 107 as described above with reference to FIG. 1.

Figure 8A:
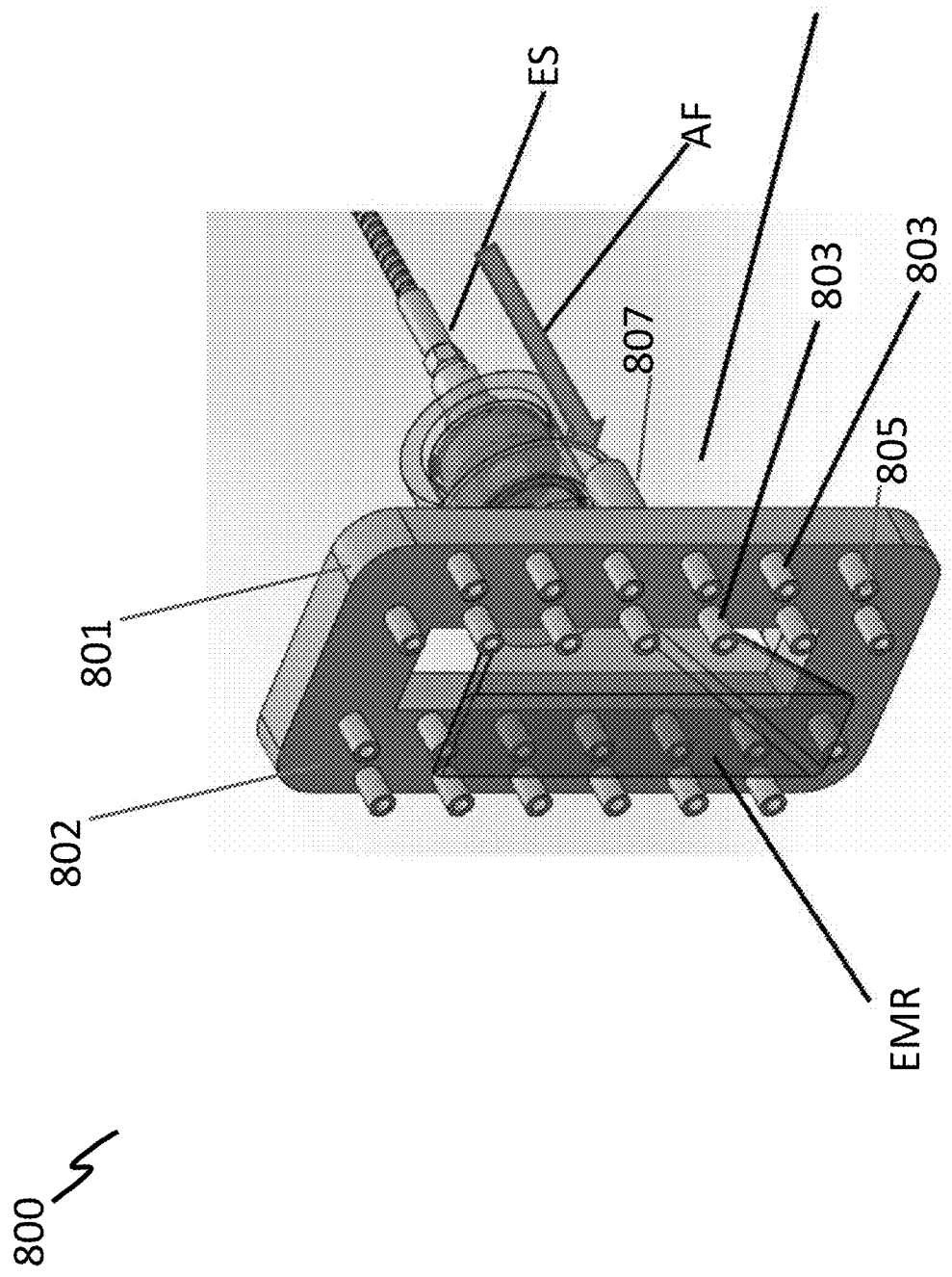
FIG. 8A is a perspective view of another rectangular jet impingement cooling apparatus in accordance with an embodiment of the present invention.
Figure 8B:
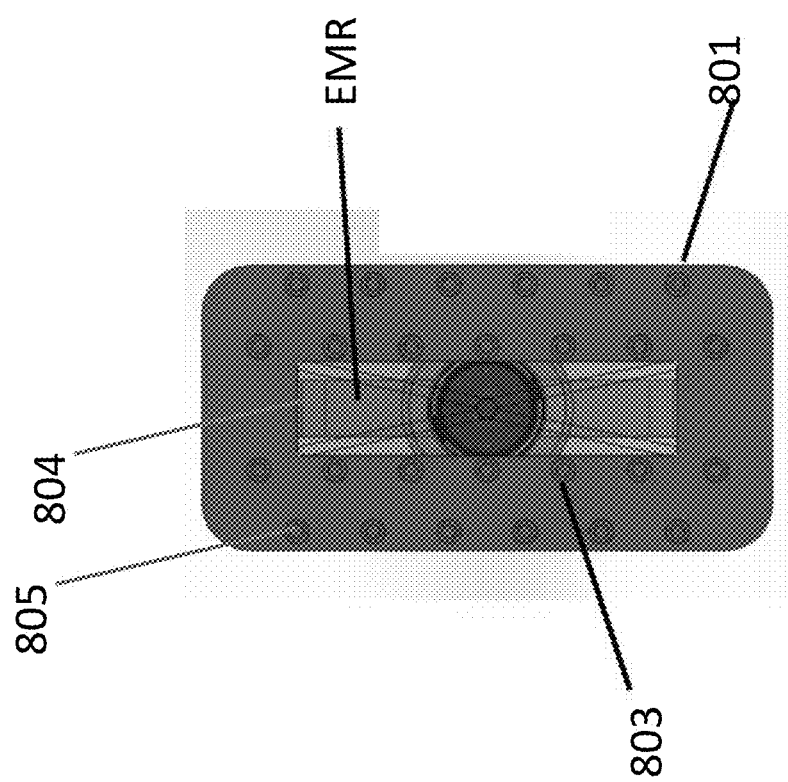
FIG. 8B is a bottom view of the rectangular jet impingement cooling apparatus of FIG. 8A in accordance with an embodiment of the present invention.

Referring now to FIG. 8A, in another embodiment, a jet impingement cooling apparatus 800 can be provided with a rectangular housing 801 to facilitate a scanning treatment pattern over a particularly large treatment area while avoiding placement of air tubes 803 in an EMR transmission region of the housing 801. In that regard, the housing 801 can include a surface 802 to be directed at a treatment area and an elongated rectangular aperture 804 defined in the housing 801 to form the EMR transmission region. To avoid placement of the air tubes within the EMR transmission region, an EMR source ES can be configured to project an expanding, elongated EMR beam through the aperture 804. Thus, because the EMR beam is an expanding beam as discussed above with reference to FIG. 6, the air tubes 803 can extend, as shown in FIG. 8B, adjacent to, but not within, the EMR transmission region and still direct the airflow through openings 805 of the air tubes 803 to impinge on the treatment area illuminated by the EMR to provide substantially uniform cooling of the treatment area. Furthermore, because additional air tubes 803 provide additional openings 805 outside of the EMR transmission region, cooling can be provided to areas adjacent to the treatment area. Such adjacent cooling can advantageously permit pre and post cooling of the treatment area when the apparatus is moved or scanned during treatment. Thus cooling can occur not only during the treatment period for a particular treatment area, but also during the dwell time for adjacent treatment areas.

In some embodiments, the apparatus 800 can further include a cold air port 807 for receiving airflow AF into the housing 801 to be directed through the openings 705. In some embodiments, each of the housing 801, the surface 802, the openings 805, and the port 807 can be, for example, substantially similar to the housing 101, surface 103, openings 105, and port 107 as described above with reference to FIG. 1. The air tubes 803 can be, for example, substantially similar to air tubes 403 as described above with reference to FIGS. 4A and 4B.

Window Cooling

In some applications, it may be desirable to prevent impingement air from impinging directly on the treatment area, for example, to prevent deformation or contamination of the treatment area. In such embodiments, the air jets exited from the openings, rather than impinging on the treatment area, can instead be configured to impinge on a transparent, thermally conductive window. In particular, the cooling heat transfer generated by impingement cooling of the window can advantageously be effective in removing heat across the entire surface of the window without interfering with EMR transmitted to the treatment area. Advantageously, cooled air flowing across the window is transparent to EMR and can thus cool the entire surface of the window. By contrast, conventional window cooling designs are limited to perimeter cooling because the fluid tubes are not transparent. Furthermore, such designs are limited in size by the thermal conductivity of the window to conduct heat to the window edges and produce uneven cooling as discussed above.

Figure 9:
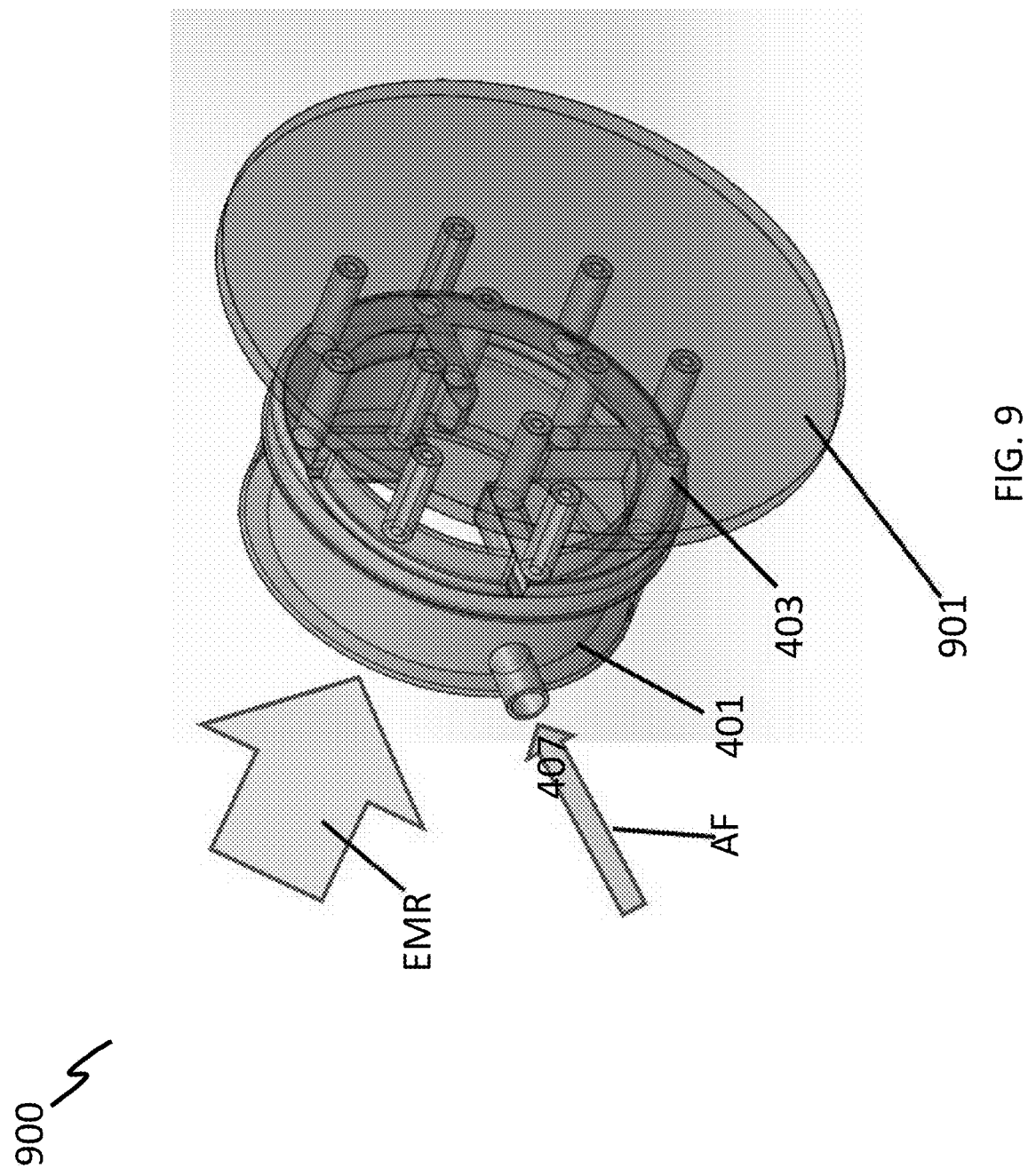
FIG. 9 is a perspective view of the jet impingement cooling apparatus of FIG. 4A having a transparent window attached thereto in accordance with an embodiment of the present invention.

Windows for cooling can be provided in any size as suitable for a particular procedure. For example, as shown in FIG. 9, a window jet impingement apparatus 900 is provided to include the jet impingement apparatus 400 of FIGS. 4A and 4B having a window 901 mounted thereto for being impinged by the airflow directed out of the openings 405 of the air tubes 403. The window 901, as shown in FIG. 9, can have a diameter larger than a diameter of the housing 401 to provide a larger cooling area on the patient to provide pre and post cooling of the treatment area as the apparatus 900 is moved between treatment areas. As appropriate to provide optical transparency and sufficient cooling, the window 901, in some embodiments, can include any suitable transparent, thermally conductive material, such as, for example, glass, optically transparent plastics, sapphire, any other suitable material, or combinations thereof.

Figure 10:
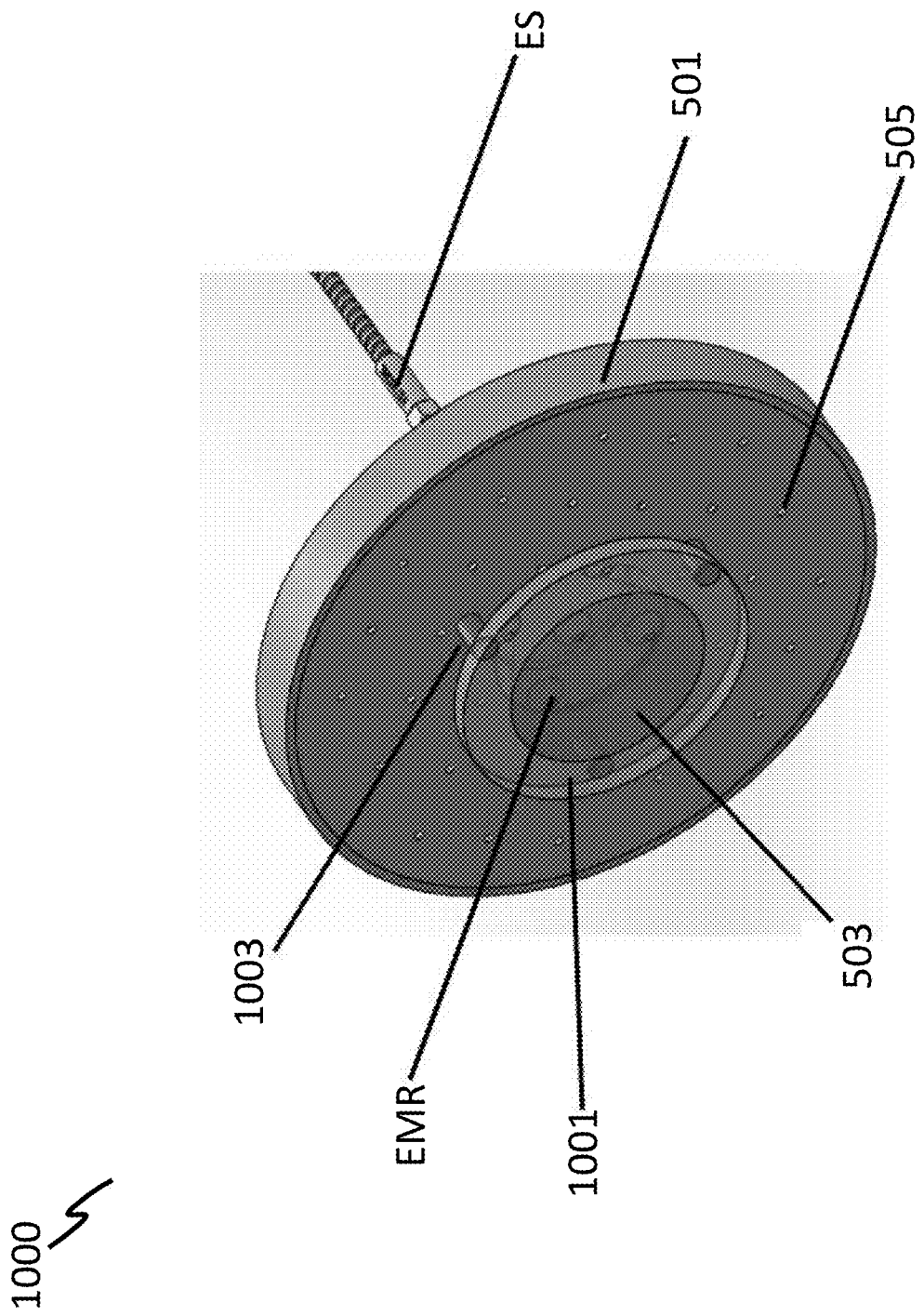
FIG. 10 is a perspective view of the jet impingement cooling apparatus of FIG. 5A having a transparent window attached thereto in accordance with an embodiment of the present invention.

Referring now to FIG. 10, a window jet impingement apparatus 1000 is provided to include the jet impingement apparatus 500 of FIGS. 5A and 5B having a window 1001 mounted thereto via mounting post 1003 for being impinged by the airflow directed out of the openings 505 of the surface 503. The window 1001, as shown in FIG. 10, can have a diameter smaller than a diameter of the housing 501 to provide window cooling in the treatment area illuminated by the EMR while still permitting direct jet impingement cooling on the patient outside of the treatment area. Thus, the apparatus can provide direct jet impingement cooling during pre and post cooling of the treatment area as the apparatus 1000 is moved between treatment areas. As appropriate to provide optical transparency and sufficient cooling, the window 1001, in some embodiments, can include any suitable transparent, thermally conductive material, such as, for example, glass, optically transparent plastics, sapphire, any other suitable material, or combinations thereof. Advantageously, a smaller window can provide a lower manufacturing cost and reduce friction between the window and the treatment area during movement of the apparatus 1000.

Figure 11:
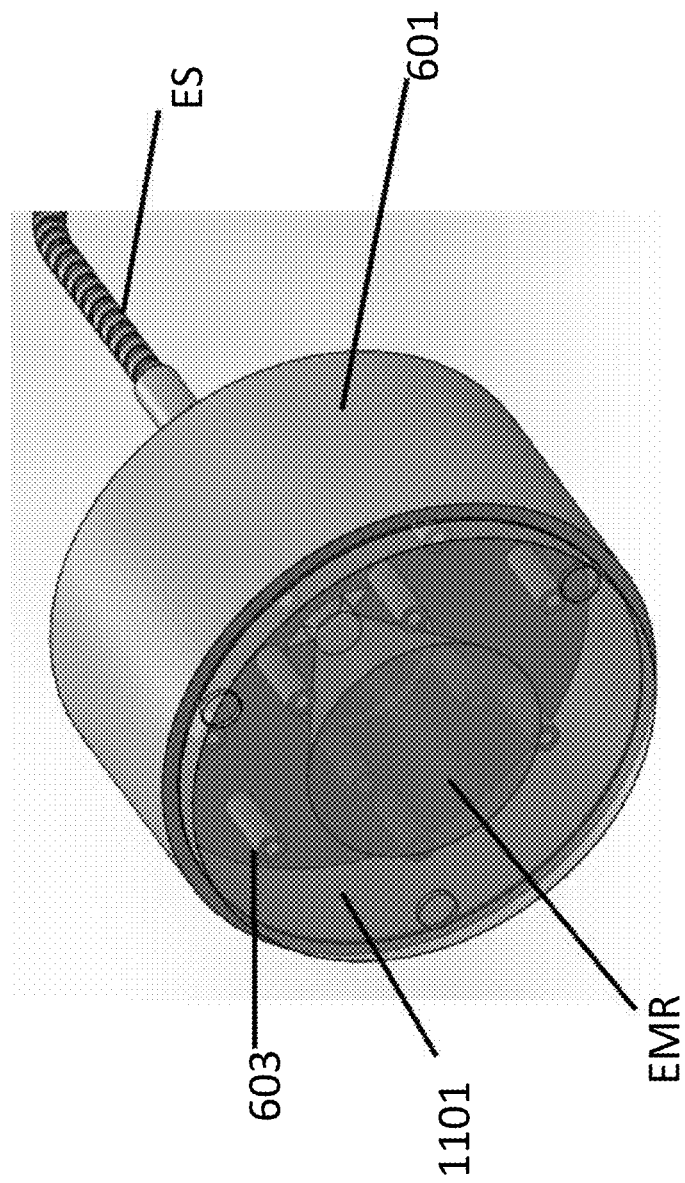
FIG. 11 is a perspective view of the jet impingement cooling of FIG. 6 having a transparent window attached thereto in accordance with an embodiment of the present invention.

Referring now to FIG. 11, a window jet impingement apparatus 1100 is provided to include the jet impingement apparatus 600 of FIG. 6 having a window 1101 mounted thereto for being impinged by the airflow directed out of the openings 605 of the air tubes 603. The window 1101, as shown in FIG. 10, can have a diameter approximately equal to a diameter of the housing 601 to provide a precise cooling area with no direct impingement on the treatment area and no pre or post cooling. Thus, the apparatus 1100 can provide a compact, maneuverable hand piece for use during treatment. As appropriate to provide optical transparency and sufficient cooling, the window 1101, in some embodiments, can include any suitable transparent, thermally conductive material, such as, for example, glass, optically transparent plastics, sapphire, any other suitable material, or combinations thereof.

Transparent Endothermic Elements

In some embodiments, an optically transparent endothermic "cold pack" may be desirable. In such embodiments, the optically transparent endothermic "cold pack" can be placed on the treatment area to provide cooling of the treatment area.

Figure 12:
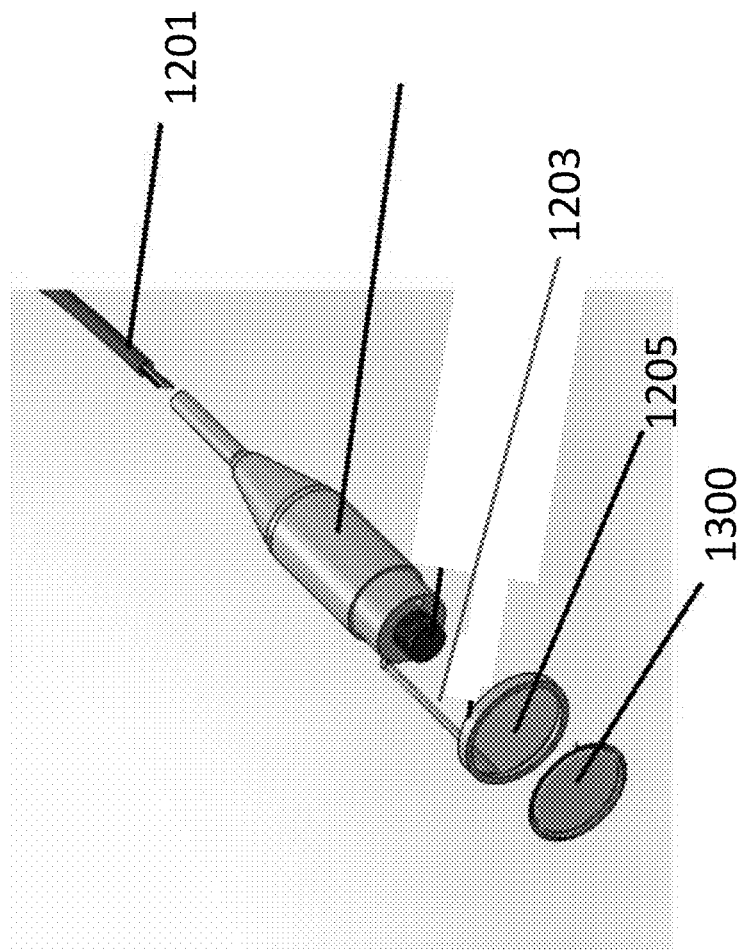
FIG. 12 is a perspective view of a cooling apparatus having a transparent endothermic cooling pack in accordance with an embodiment of the present invention.

Referring now to FIG. 12, a cooling apparatus 1200 having a transparent endothermic cooling pack 1300 is provided for providing a treatment while cooling a treatment area. In one embodiment, the cooling apparatus 1200 can include an EMR source 1201 for providing treatment to the treatment area. In some embodiments, the EMR source 1201 can include, for example, a laser source, an RF source, a fiber optic cable, a laser collimator, a flashlamp source, an x-ray source, any other suitable source of EMR, or combinations thereof. The cooling apparatus 1200 can also include a spacing element 1203 for maintaining a preferred distance between the EMR source 1201 and the treatment area. The spacing element 1203 can include any suitable structure capable of maintaining a separation between the EMR source 1201 and the treatment area, including, for example, a rod as shown in FIG. 12. The cooling apparatus 1200 can also include a receiver 1205 for receiving and removably retaining the endothermic cooling pack 1300 against the treatment area to provide cooling to the treatment area.

Figure 13:
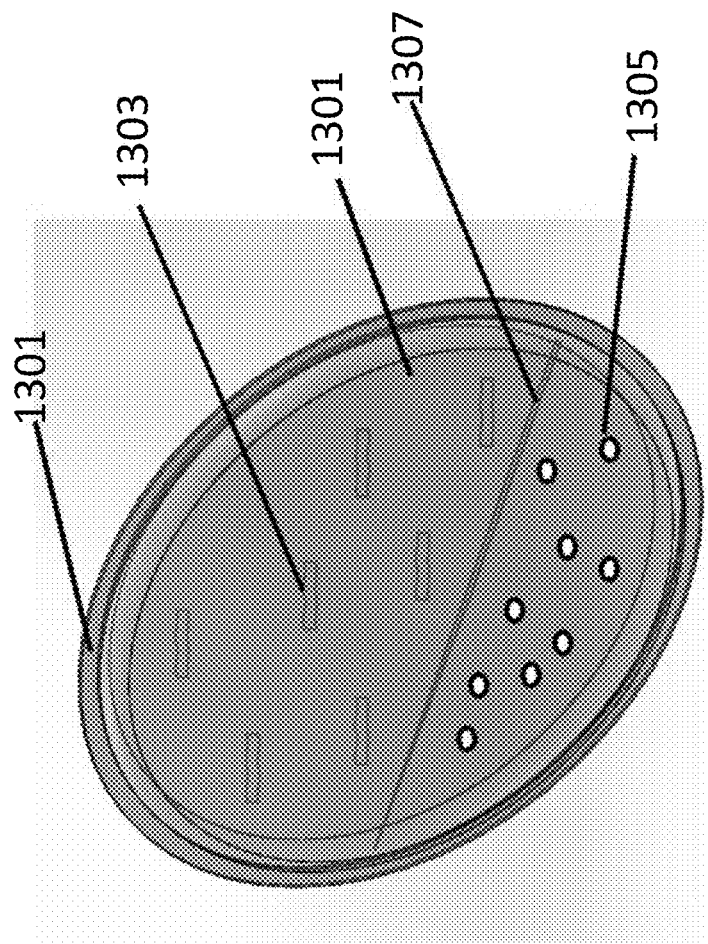
FIG. 13 is a perspective view of a transparent endothermic cooling pack in accordance with an embodiment of the present invention.

Referring now to FIG. 13, the cooling pack 1300, in some embodiments, can include an outer pack 1301 which can be constructed of any suitable material for retaining reagents therein, such as, for example, optically transparent plastics, glass, acrylics, polyethylenes, celluloses, polyvinyls, any other suitable optically transparent material, or combinations thereof. In some embodiments, the cooling pack 1300 can be filled with any two or more reagents 1303, 1305 suitable for producing an endothermic reaction having optically transparent reagents and products. For example, in one embodiment, sodium thiosulphate salt has optically transparent crystals and, in solution with water, provides good optical transmission. However, it will be apparent that any other suitable materials with similar properties and clear solution can be used in some embodiments. In some embodiments, a breakable or crushable plastic or glass divider 1307 can be provided to keep the reagents 1303, 1305 separate until the pack 1300 is to be used, whereupon the divider 1307 can be broken to bring the reagents 1303, 1305 into contact to begin the endothermic reaction.

In general, the cold pack 1300 can produce an endothermic reaction lasting a sufficient time to provide treatment to a treatment area, although in some applications it may be necessary to stop the procedure and replace the cold pack 1300 to provide sufficient cooling time for treatment. The cold pack 1300, can also be designed to maintain a thickness narrow enough to prevent deleterious EMR energy attenuation. In general, such attenuation can be avoided for cold packs 1300 having a total filled thickness of about 1 cm or less. In general, the thickness is dictated by a volume of the reagents 1303, 1305 provided in the cold pack 1300. However, in some embodiments, in order to provide a controlled, consistent thickness throughout the cold pack 1300, the cold pack 1300 can include one or more plastic spacer structures (not shown) or the solution can include optically clear free particles (not shown) having a predetermined thickness. For example, in some embodiments, clear plastic spheres having a 5 mm diameter can be included. In such embodiments, in order to maximize reagent content, the outer pack 1301 can be constructed of a very thin material. For example, in some embodiments, the outer pack 1301 material can have a thickness between about 0.003 inches to about 0.015 inches. Additionally, such thin outer pack 1301 material helps promote full contact with the treatment area by providing a compliant surface for conforming to any contours of the treatment area.

Figure 14:
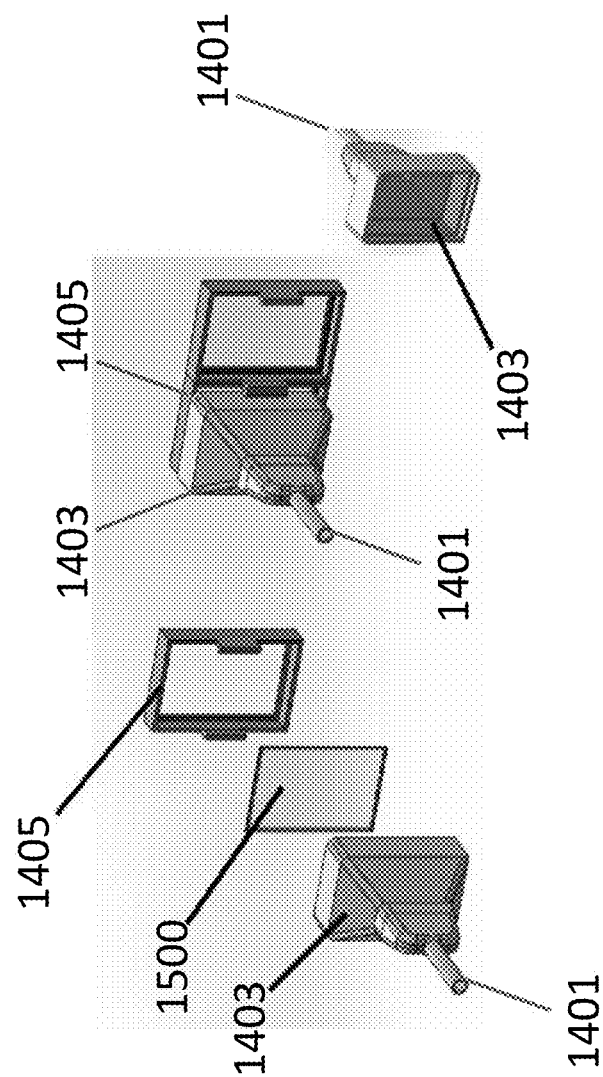
FIG. 14 is a perspective view of another cooling apparatus having another transparent endothermic cooling pack in accordance with an embodiment of the present invention.

Referring now to FIG. 14, to the extent that cooling over a larger area is desired, a cooling apparatus 1400 having a rectangular transparent endothermic cooling pack 1500 is provided for providing a treatment while cooling a treatment area. In some embodiments, the apparatus 1400 can include an EMR source 1401 for providing treatment to the treatment area. In some embodiments, the EMR source 1401 can include, for example, a laser source, an RF source, a fiber optic cable, a laser collimator, a flashlamp source, an x-ray source, any other suitable source of EMR, or combinations thereof. The cooling apparatus 1400 can also include a spacing element 1403 for maintaining a preferred distance between the EMR source 1401 and the treatment area. The spacing element 1403 can include any suitable structure capable of maintaining a separation between the EMR source 1401 and the treatment area, including, for example, a rectangular pyramid shaped spacer as shown in FIG. 12. The cooling apparatus 1400 can also include a receiver 1405 configured to receive and removably retain the rectangular endothermic cooling pack 1500 against the treatment area to provide cooling to the treatment area. In general, the receiver 1405 can be, for example, substantially similar to the receiver 1205 described above with reference to FIG. 12.

Figure 15:
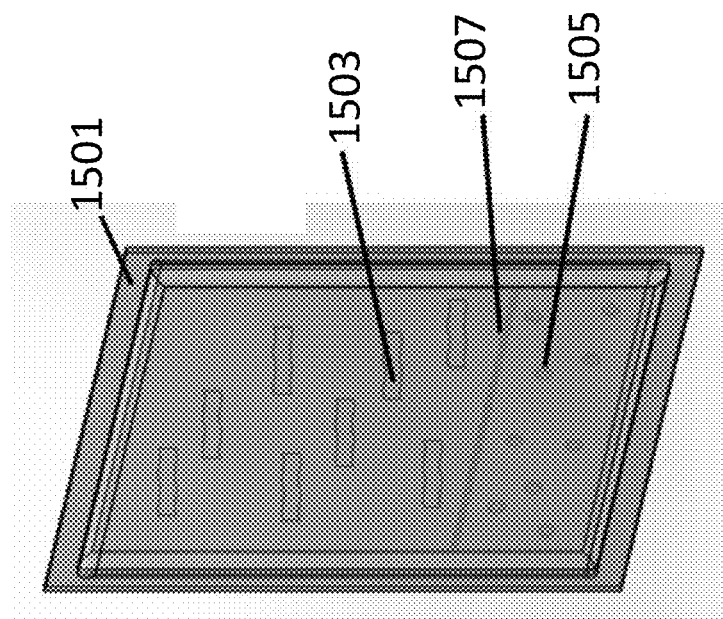
FIG. 15 is a perspective view of another transparent endothermic cooling pack in accordance with an embodiment of the present invention.

Referring now to FIG. 15, the rectangular cooling pack 1500 can include an outer pack 1501, reagents 1503, 1505, and a divider 1507. Each of the outer pack 1501, the reagents 1503, 1505, and the divider 1507 can be substantially similar, for example, to the outer pack 1301, the reagents 1303, 1305, and the divider 1307 described above with reference to FIG. 13.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A method for cooling a target region, the method comprising:
    continuously directing a fluid flow from a treatment device to a first treatment area of the target region to provide cooling to the first treatment area, the fluid flow passing through a plurality of openings on an optically transparent region of a window of the treatment device;
    exposing the first treatment area to electromagnetic radiation (EMR) being directed from the treatment device through at least one opening on the optically transparent region of the window and through at least a portion of the optically transparent region of the window; and
    automatically moving the treatment device with an automated mechanism from the first treatment area to a second treatment area of the target region.

2. The method of claim 1, wherein the automated mechanism is programmed to deliver an appropriate amount of EMR to maintain a target temperature range in the target region.

3. The method of claim 1, wherein the fluid flow exiting each opening of the plurality of openings has a velocity of 20 to 200 meters per second.

4. The method of claim 1, wherein the fluid flow exiting each opening of the plurality of openings has a velocity sufficient to minimize a thermal boundary layer formed on the treatment area.

5. The method of claim 1, wherein the fluid is transparent to the EMR.

6. The method of claim 1, wherein the EMR is light radiation.

7. A method for cooling a surface of a treatment area, the method comprising:
    continuously providing a fluid flow along a pathway of a treatment device, the pathway terminating in a window having an optically transparent region provided with a plurality of openings through which fluid flow can exit to create a plurality of impingement jets, each impingement jet having a fluid flow velocity;
    positioning the treatment device to direct the impingement jets towards the surface thereby creating a free jet region and an impingement region with a boundary layer between the window and the surface;
    exposing the surface to electromagnetic radiation (EMR) being directed from the treatment device through at least one opening on the optically transparent region of the window and through at least a portion of the optically transparent region of the window; and cooling the surface by maintaining the velocity at a range selected to minimize the boundary layer.

8. The method of claim 7, wherein the velocity range is 20 to 200 meters per second.

9. The method of claim 7, wherein the treatment area is a first treatment area of a target region, the method further comprising:
   automatically moving the treatment device with an automated mechanism from the first treatment area to a second treatment area of the target region, wherein the impingement jets do not interfere with the EMR.

10. The method of claim 9, wherein the fluid is transparent to EMR.

11. The method of claim 9, wherein the EMR is light radiation.

12. The method of claim 7, wherein positioning further comprises maintaining a distance between the window and the surface.

13. The method of claim 12, wherein the distance is between 0.001 and 1 inches.

14. A method for cooling a target region, the method comprising:
   continuously providing a fluid flow along a pathway of a treatment device, the pathway terminating in a window having an optically transparent region provided with a plurality of openings through which fluid flow can exit to create a plurality of impingement jets, each impingement jet having a fluid flow velocity;
   positioning the treatment device to direct the impingement jets towards a surface of a first treatment area of the target region thereby creating a free jet region and an impingement region with a boundary layer between the window and the surface;
   exposing the surface to electromagnetic radiation (EMR) being directed from the treatment device through at least one opening on the optically transparent region of the window and through at least a portion of the optically transparent region of the window;
   cooling the surface by maintaining the velocity at a range selected to minimize the boundary layer; and
   automatically moving the treatment device with an automated mechanism from the first treatment area to a second treatment area of the target region.

15. The method of claim 14, wherein the velocity is between 20 and 200 meters per second.

16. The method of claim 14, wherein the fluid is transparent to EMR.

17. The method of claim 14, wherein the EMR is light radiation.

18. The method of claim 14, wherein positioning further comprises maintaining a distance between the window and the surface.

19. The method of claim 18, wherein the distance is between 0.001 and 1 inches.

20. The method of claim 14, wherein the automated mechanism is programmed to deliver an appropriate amount of EMR to maintain a target temperature range in the target region.

* * * * *